United States Patent
Bello et al.

(10) Patent No.: US 10,242,895 B2
(45) Date of Patent: Mar. 26, 2019

(54) SELF-CONTAINED METROLOGY WAFER CARRIER SYSTEMS

(71) Applicant: GLOBALFOUNDRIES Inc., Grand Cayman (KY)

(72) Inventors: Abner Bello, Clifton Park, NY (US); Stephanie Waite, Glens Falls, NY (US); William J. Fosnight, Saratoga Springs, NY (US); Thomas Beeg, Gansevoort, NY (US)

(73) Assignee: GLOBALFOUNDRIES Inc., Grand Cayman (KY)

( * ) Notice: Subject to any disclaimer, the term of this patent is extended or adjusted under 35 U.S.C. 154(b) by 0 days.

(21) Appl. No.: 15/876,472

(22) Filed: Jan. 22, 2018

(65) Prior Publication Data

US 2018/0143077 A1 May 24, 2018

Related U.S. Application Data

(63) Continuation of application No. 15/193,502, filed on Jun. 27, 2016, now Pat. No. 9,911,634.

(51) Int. Cl.
*G01J 5/00* (2006.01)
*H01L 21/673* (2006.01)
(Continued)

(52) U.S. Cl.
CPC ........ *H01L 21/6732* (2013.01); *G01J 5/0007* (2013.01); *G01J 5/025* (2013.01); *G01N 21/211* (2013.01); *G01N 21/55* (2013.01); *G01R 27/00* (2013.01); *H01L 21/67253* (2013.01); *H01L 21/67353* (2013.01); *H01L 21/67386* (2013.01); *H01L 22/12* (2013.01); *G01J 5/0825* (2013.01); *G01J 5/0896* (2013.01); *G01N 2201/0683* (2013.01); *G01N 2201/06113* (2013.01); *G01N 2201/12* (2013.01); *G05B 2219/37224* (2013.01); *H01L 21/67745* (2013.01)

(58) Field of Classification Search
CPC ................... H01L 21/67745; H01L 21/67253
See application file for complete search history.

(56) References Cited

U.S. PATENT DOCUMENTS 3,848,188 A 11/1974 Ardezzone et al.
5,837,986 A * 11/1998 Barile .................... G06F 3/002
235/462.01
(Continued)

OTHER PUBLICATIONS

U.S. Appl. No. 15/233,454, filed Aug. 10, 2016, titled "Recharable Wafer Carrier Systems".

*Primary Examiner* — Kiho Kim
(74) *Attorney, Agent, or Firm* — Thompson Hine LLP; Francois Pagette

(57) ABSTRACT

A self-contained metrology wafer carrier systems and methods of measuring one or more characteristics of semiconductor wafers are provided. A wafer carrier system includes, for instance, a housing configured for transport within the automated material handling system, the housing having a support configured to support a semiconductor wafer in the housing, and a metrology system disposed within the housing, the metrology system operable to measure at least one characteristic of the wafer, the metrology system comprising a sensing unit and a computing unit operably connected to the sensing unit. Also provided are methods of measuring one or more characteristics of a semiconductor wafer within the wafer carrier systems of the present disclosure.

19 Claims, 8 Drawing Sheets

(51) Int. Cl.
  _H01L 21/66_ (2006.01)
  _G01N 21/55_ (2014.01)
  _G01N 21/21_ (2006.01)
  _G01J 5/02_ (2006.01)
  _G01R 27/00_ (2006.01)
  _H01L 21/67_ (2006.01)
  _G01J 5/08_ (2006.01)
  _H01L 21/677_ (2006.01)

(56) References Cited

U.S. PATENT DOCUMENTS

| | | | |
|---|---|---|---|
| 5,963,315 A * | 10/1999 | Hiatt | H01L 21/67745 356/237.3 |
| 6,798,513 B2 | 9/2004 | Abraham | |
| 6,884,639 B2 | 4/2005 | Dougan et al. | |
| 7,106,425 B1 | 9/2006 | Bultman et al. | |
| 9,064,406 B1 * | 6/2015 | Stevens | G08G 1/00 |
| 2002/0101508 A1 | 8/2002 | Pollack | |
| 2002/0118365 A1 | 8/2002 | Kessel et al. | |
| 2003/0001083 A1 | 1/2003 | Corrado et al. | |
| 2003/0002043 A1 * | 1/2003 | Abdulhalim | G03F 7/70633 356/400 |
| 2007/0229833 A1 | 10/2007 | Rosencwaig et al. | |
| 2008/0305563 A1 | 12/2008 | Ko et al. | |
| 2010/0049353 A1 | 2/2010 | Takizawa et al. | |
| 2011/0001971 A1 | 1/2011 | Iwanami et al. | |
| 2013/0258093 A1 * | 10/2013 | Jingu | G01N 21/9501 348/92 |
| 2015/0006103 A1 | 1/2015 | De Wel et al. | |
| 2017/0372924 A1 | 12/2017 | Bello et al. | |

* cited by examiner

SELF-CONTAINED METROLOGY WAFER CARRIER SYSTEMS

CROSS-REFERENCE TO RELATED APPLICATION

This patent application is a continuation of U.S. patent application Ser. No. 15/193,502, filed Jun. 27, 2016, entitled "Self-Contained Metrology Wafer Carrier Systems," the entire subject matter of this application being incorporated herein by reference.

FIELD OF THE DISCLOSURE

The present disclosure relates to semiconductor wafer carrier systems, and more particularly, to self-contained metrology wafer carrier systems.

BACKGROUND OF THE DISCLOSURE

In an automated fabrication plant setting (commonly referred to as "fab"), wafers are contained in a wafer carrier which is transported between stations via an automated material handling system (AMHS). A station could be a process tool to deposit or to etch films, or a metrology tool to measure characteristics of the films. A wafer carrier in an automated fab is also known as a front opening unified pod and is commonly referred to as a FOUP. A FOUP is typically formed of a specialized plastic housing, which is designed to hold semiconductor wafers securely and safely in a protective environment. A FOUP includes a front opening section which allows the wafers to be inserted therein and removed therefrom for processing.

A significant amount of time can be incurred in transporting the FOUP from station to station, particularly if the automated fabrication plant is large or if there are numerous steps in completing the manufacturing process. Typically, after processing the wafer at a station, the FOUP including the processed wafers, are transported to a metrology station for measurement. Often, after further transporting and processing of the wafers at each subsequent station, the FOUP is transported to the metrology station for further measurement. Additionally, metrology equipment is expensive and occupies cleanroom floor space.

SUMMARY OF THE DISCLOSURE

The shortcomings of the prior art are overcome and additional advantage are provided through the provisions of a FOUP having a metrology system integrated therein. In one embodiment of the disclosure, a semiconductor wafer carrier system for an automated material handling system includes, for instance, a housing configured for transport within the automated material handling system, and a metrology system disposed within the housing. The metrology system has, for example, a sensing unit and a computing unit operably connected to the sensing unit. The housing has, for example, a support for supporting a wafer in the housing. The metrology system is operable to measure at least one characteristic of the wafer while the wafer is in the housing.

In another embodiment, a method for measuring one or more characteristics of a semiconductor wafer is provided. The method includes, for instance, providing a wafer in a wafer carrier system for an automated material handling system, determining in the wafer carrier system a measurement of at least one characteristic of the wafer, and transmitting the determined measurement of at least one characteristic of the wafer from the wafer carrier system to a remote location. The determining a measurement may occur at a processing station, during transport between stations, during transport between a station and a storage unit, and/or while in a storage unit. The measurement of at least one characteristic of the wafer may be transmitted wirelessly to a remote location.

The system may include a power source for powering the sensing unit or sensor and the computing unit within the housing. The power source may include a battery. The system may also include a network adapter operably connected to the computing unit within the housing. The system may also include a wireless transmitter for transmitting the at least one characteristic of the wafer measured by the sensing unit transmits such information to a communication network. The metrology system may be located within the housing within an integrated tool or enclosure. The sensing unit may be capable of measuring film thickness, film temperature, distribution of heat on the wafer, film composition, electrical conductivity, film optical constants, optical images, surface roughness, wafer topography, wafer bow, defects on the wafer surface, number of particles on the wafer surface, and/or reflectivity of a surface of the wafer. The sensing unit may be an ellipsometer, optical camera, reflectometer and/or a pyrometer. The sensing unit may include at least one probe operably connected to the computing unit which may be used to measure at least one of the aforementioned characteristics of the wafer, or multiple of such characteristics. The sensing unit may include a multiplexor operably connected to the computing unit, and a plurality of probes may be operably connected to the multiplexor. The probes may be operable for use in measuring at least one or more, or all of the aforementioned characteristics of the wafer.

The sensing unit may include an emitting portion, or emitter. The emitter may include, for example, a laser, a polarizer connected to the laser, and a focuser operably connected to the polarizer. The sensing unit may also include, for example, a collecting portion which may further include a detector, an analyzer operably connected to the detector, and a lens connector operably connected to the analyzer. The focuser and lens connector are used to measure a portion of the wafer.

The sensing unit may include an emitter, or emitting portion, a collector, or collecting portion, and a multiplexor operably connected to the emitter and collector, useable in measuring at least one of the aforementioned characteristics of the wafer at a particular location or portion of the wafer.

The system may include a transmitter which transmits the measured one or more of the aforementioned characteristics of the wafer to a remote computer. The transmitter may be a wireless transmitter. The transmission of information may be wirelessly transmitted from the wafer carrier system to a remote location. This system may conduct measurements at different times during the wafer handling or transport system. The measurement may occur at a particular processing station for the wafer, or during transport between processing station, or during transport between a station and a storage unit, and/or while in a storage unit.

Additional features and advantages are realized through the principles of the present disclosure. Other embodiments of the disclosure are described in detail herein and are considered to be part of the claimed disclosure.

BRIEF DESCRIPTION OF THE DRAWINGS

One or more embodiments of the present disclosure are particularly pointed out and distinctly claimed as examples in the claims at the conclusion of the specification. The foregoing and other objects, features, and advantages of the disclosure are apparent from the following detailed description taken in conjunction with the accompanying drawings in which:

DETAILED DESCRIPTION OF THE DISCLOSURE

Figure 1:
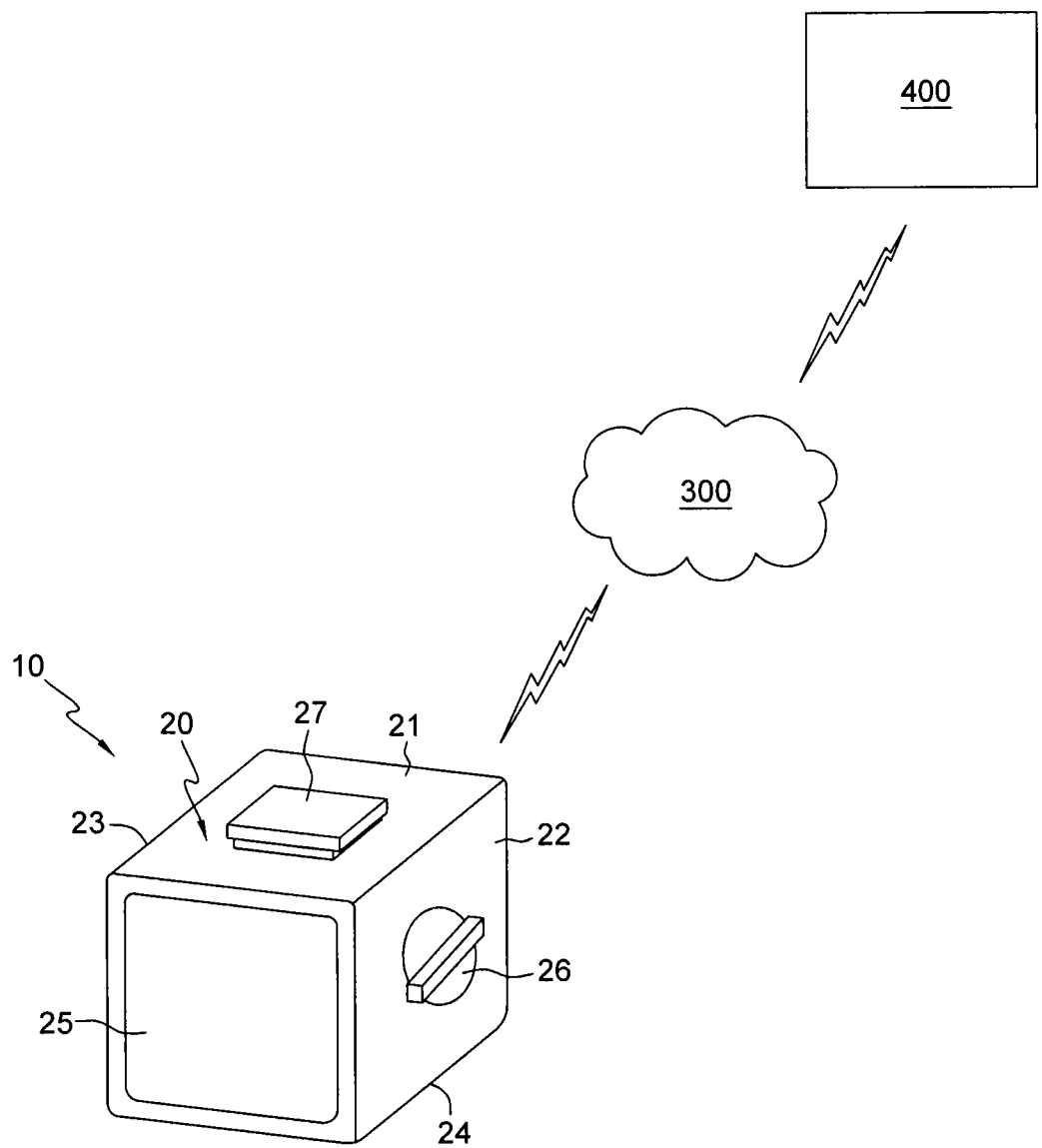
FIG. 1 is a schematic illustration of a wafer carrier system according to an embodiment of the present disclosure.

The present disclosure and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the disclosure in detail. It should be understood, however, that the detailed description and the specific examples, while indicating embodiments of the disclosure, are given by way of illustration only, and are not by way of limitation. Various substitutions, modifications, additions and/or arrangements within the spirit and/or scope of the underlying concepts will be apparent to those skilled in the art from this disclosure. Note that these figures are not drawn to scale in order to facilitate understanding of the disclosure, and that the same reference numerals used throughout different figures designate the same or similar elements.

Wafer carrier systems of the present disclosure may include a self-contained metrology system for measuring one or more characteristics of a wafer or wafers contained in the carrier or FOUP, for example, after processing at a station and prior to processing at the next station. For example, wafer carrier systems of the present disclosure may be used with and transported by, for example, an automated transport system such as an automated material handling system (AMHS) in place in an automated fabrication plant, commonly referred to as a fab. As will be appreciated, wafer carrier systems of the present disclosure may have self-contained metrology instruments and may avoid the need to transport the wafers to a separate metrology station.

FIGS. 1-10 depict, by way of example, embodiments of wafer carrier systems and methods in accordance with one or more embodiments of the present disclosure. The semiconductor wafer, generally denoted 80 (FIGS. 2A, 2B, and 3), 180 (FIGS. 4 and 5) and 280 (FIG. 6), may be an intermediate device undergoing processing steps.

FIG. 1 illustrates a wafer carrier system 10 according to one embodiment of the present disclosure, which may communicate wirelessly, for instance, via a communication network 300 to transmit data and control commands to a remote computer 400. Wafer carrier system 10 may generally include a housing 20 that has a top wall 21, side walls 22, 23, a bottom wall 24, a rear wall (not shown), and a front wall 25, which may also be referred to as a front door. Housing 20 may also include an adaptor 27 and handles 26 for use with or engageable with an automated transport system, for example, AMHS or robots. Housing 20 may include additional features that allow it to function in an automated fab.

For example, housing 20 may include an adaptor 27 operably connected to a robot or engageable with an AMHS for transporting wafer carrier system 10 from one station to the next. For example, wafer carrier system 10 may be transported from a first station to a second station, to a third station, to a fourth station, and so forth. Wafer carrier system 10 may be operable with an existing AMHS in an automated fab environment.

Figure 2A:
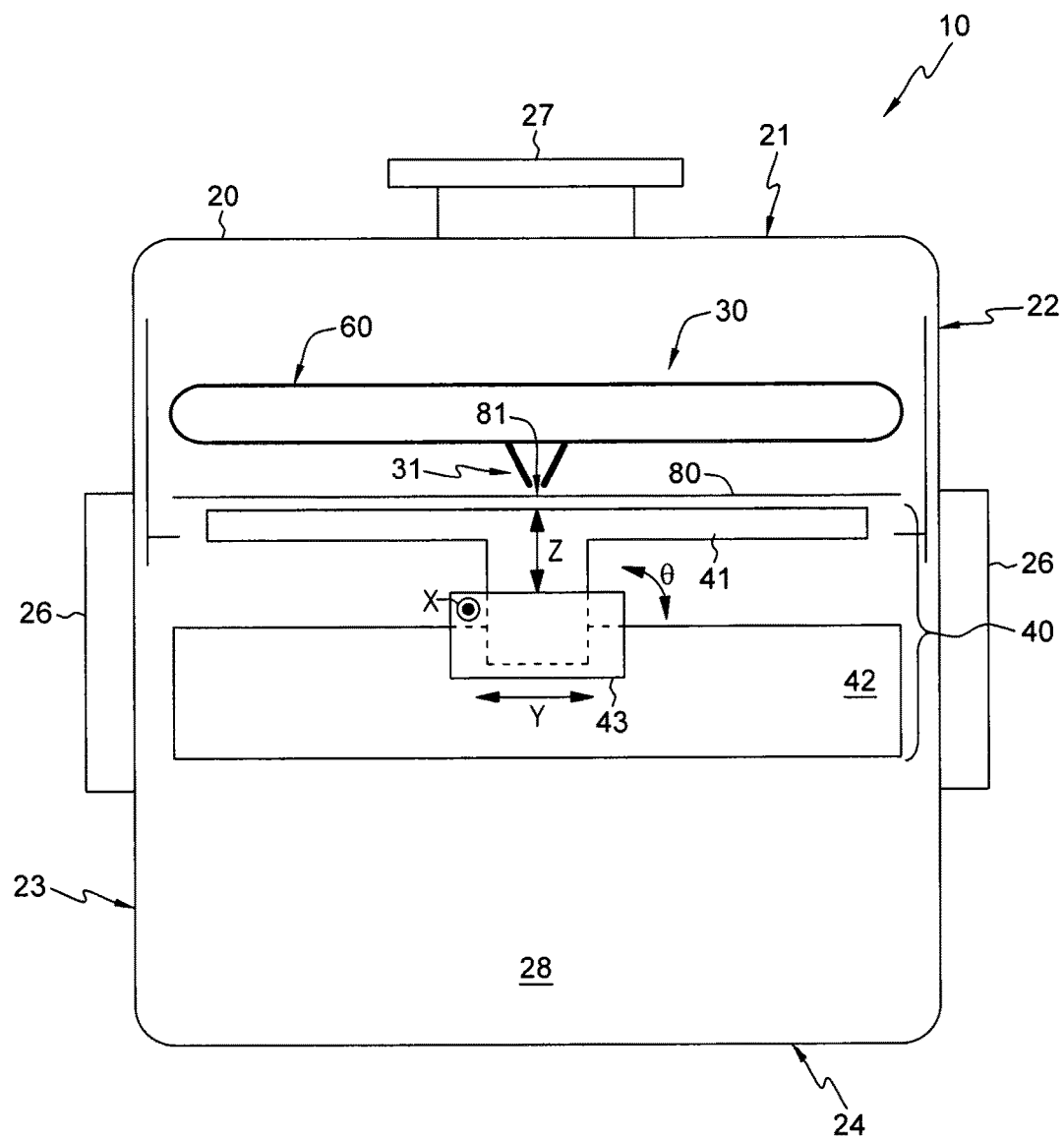
FIG. 2A is an enlarged cross-sectional front view of the wafer carrier system of FIG. 1.
Figure 2B:
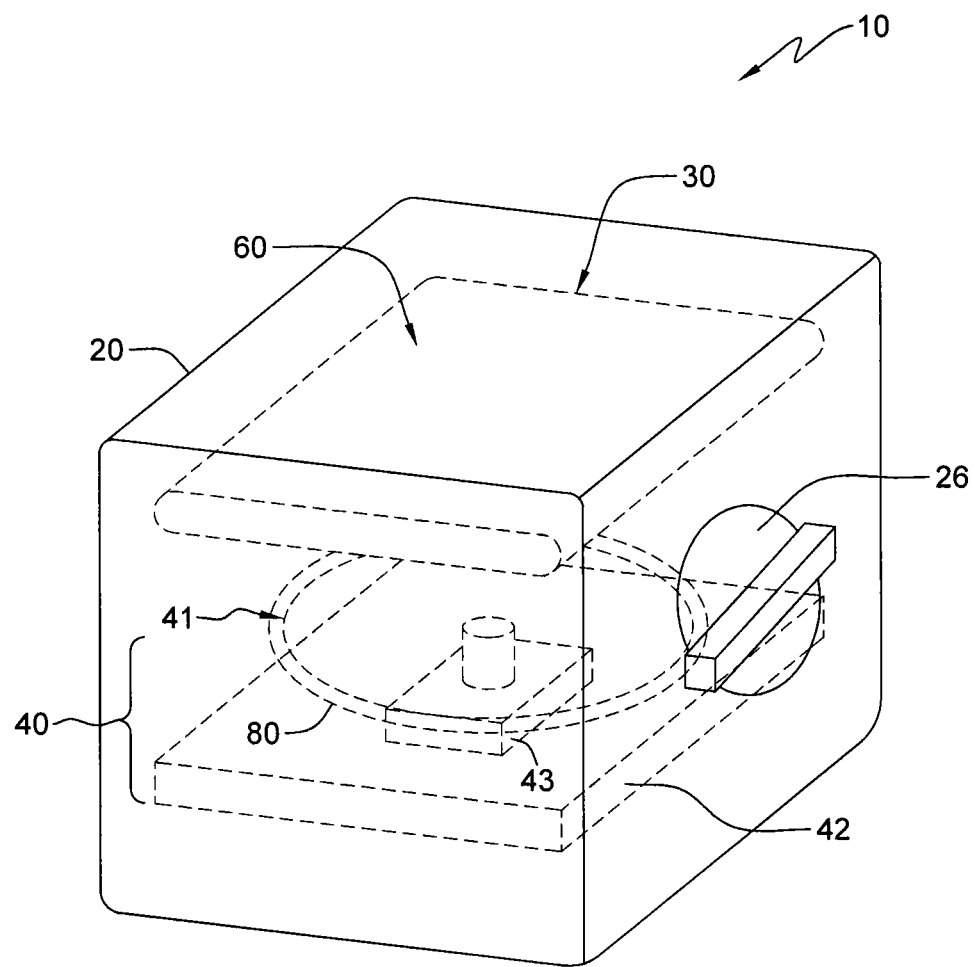
FIG. 2B is an orthogonal view of the wafer carrier system of FIG. 1.

With reference to FIG. 2A, wafer carrier system 10 may generally include housing 20, a metrology system 30 disposed within housing 20, and a support 40 for supporting a semiconductor wafer 80 in housing 20. Housing 20 may include an inner chamber 28. Metrology system 30 may include a metrology tool or enclosure 60 disposed within housing 20. Enclosure 60 is not limited to a box-like configuration and may be any structure that allows for one or more components of metrology system 30 to be secured onto it for measuring one or more characteristic of wafer 80. For instance, metrology tool or enclosure 60 may be a wholly enclosed structure or may be a supporting frame, such as a chassis. Support 40 may be any structure that holds a wafer in place within housing 20 for measurement. For example, support 40 may include, for example, a platform 41 and a base 42. As also illustrated in FIG. 2B, base 42 may be operably connected to the bottom of platform 41. Base 42 may also be operably connected to the side of platform 41 (not shown). Platform 41 may be referred to as, for example, a chuck, and base 42 may be referred to as, for example, a stage. Platform 41, i.e. the chuck, may provide a surface for the placement of the wafer 80 being measured. Base 42, i.e. stage, may be positioned below the platform and may include a micro z-motion motor 43 to provide z-motion in the direction of double headed arrow Z (FIG. 2A) to the platform and to the wafer being measured. The platform, in one embodiment, translates in the Z-direction toward metrology system 30 to move wafer 80 towards the metrology system 30 to allow for measurement of the wafer 80. The motor may be connected to a mechanism which allows platform 41 and base 42 to move relative to one another so as to move wafer 80 towards and away from metrology system 30. Suitable mechanism may include linear screws or any other suitable mechanism. The base 42 may include other micro motion motors, for instance, a micro x-motion motor, a micro y-motion motor, and/or a micro θ-motion motor to provide x-motion in a forward and back direction as depicted by double circle, i.e. a solid circle within a circle, X (FIG. 2A), y-motion in the direction of double headed arrow Y (FIG. 2A), and/or θ-motion in the direction of double headed arrow θ (FIG. 2A), respectively. The platform and the base may be made of any suitable material, for example, the same materials used for the housing. Other supports for supporting one or more wafers may include brackets, or other supports attached to the inner sidewalls of the housing. Housing 20 may be referred to as a wafer carrier or a FOUP, and housing 20 may be any acceptable FOUP, i.e. any FOUP that meets the appropriate standard. The above detailed components may be mounted or otherwise secured to housing 20.

Metrology system 30 disposed in wafer carrier system 10 may be any metrology instrument or measurement tool for measuring one or more characteristics of a wafer. The one or more characteristics of a wafer measured may include film thickness, film temperature, distribution of heat on the wafer, film composition, electrical conductivity, reflectivity of a surface of the wafer, film optical constants, surface roughness, wafer topography, wafer bow, defects on the wafer surface, number of particles on the wafer surface, other characteristics, and the like.

With reference still to FIG. 2A, metrology system 30 may include enclosure 60 within housing 20, and may include in this embodiment, a sensing unit 31 as described in greater detail below.

Figure 3:
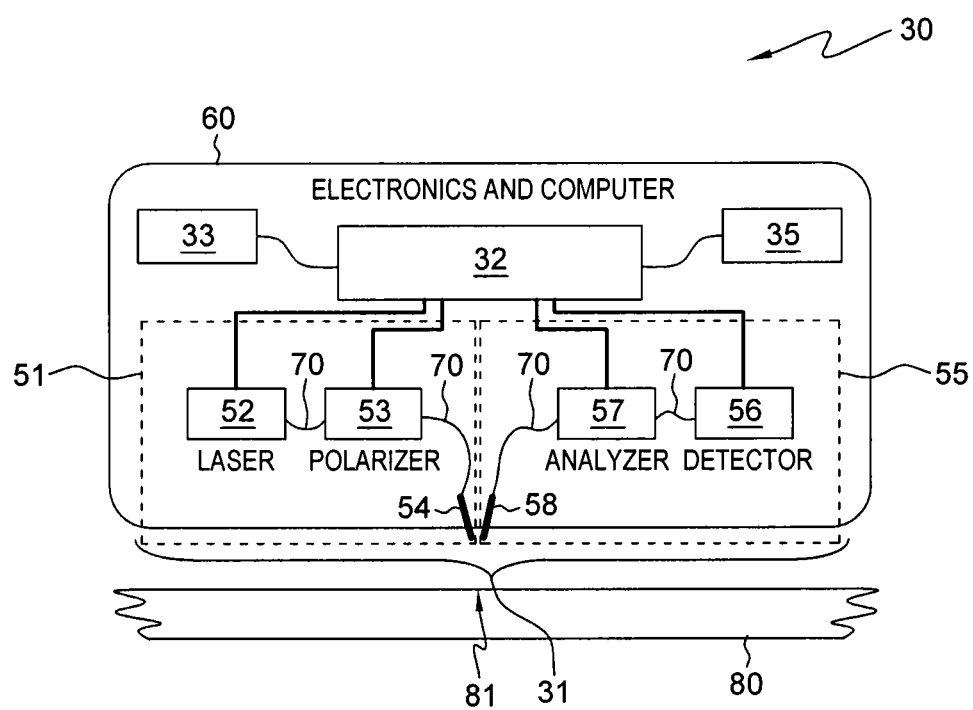
FIG. 3 is a schematic illustration of the metrology system of FIG. 2A.

As shown in FIG. 3, metrology system 30 may include, for instance, a metrology tool or equipment, for example, an ellipsometer. Metrology system 30 may include sensor or sensing unit 31 such as an optical system, a computer or computing unit 32 connected to the sensing unit 31, and a power source 33 that powers the computing unit 32 and the sensing unit 31. Computing unit 32 may be a computing system or other computing device that includes any appropriate hardware component(s) capable of implementing functions, as described in greater detail below. Metrology system 30 may also include a network adaptor 35 for communication of data between computing unit 32 and another component, such as another computing unit or computer system, across communication links. Network adaptor 35 may be, for instance, a transmitter, and may be capable of sending and receiving data and control commands. For instance, after measuring one or more characteristics of a wafer, the measurement data may be transmitted, for example, wirelessly to a remote computer 400 (FIG. 1). Transmission of measurement data is not limited to wireless transmission and may be transmitted in any conventional manner. For instance, wafer carrier system 10 (FIG. 1) may be, for example, docked at a station for transfer of data. Network adaptor 35 may be a part of computing unit 32, for example, as an integrated component of computing unit 32 such as a network interface card (NIC) or a wireless NIC, or may be operably connected to computing unit 32.

Metrology system 30 may also include additional components, such as wiring and standard connectors and fittings for the operations and functions of metrology system 30, which will be apparent to one skilled in the arts. Metrology system 30 may be assembled in any operable manner, for instance, without requiring any particular alignment or layout using, for example, appropriate connectors, adaptors, and/or wiring. While power source 33 and network adaptor 35 are described and illustrated as being within enclosure 60, it will be appreciated that power source 33 and network adaptor 35 may independently be disposed outside enclosure 60 but within housing 20 of wafer carrier system 10, and operably connected or connectable to computing unit 32. Power source 33 may be, for example, a battery, which may be, for instance, rechargeable.

As illustrated in FIG. 3, one embodiment of sensing unit 31 may include, for example, an emitting portion 51 and a collecting portion 55. Emitting portion 51 may include an emitter 52 such as a laser connected to a polarizer 53, with the polarizer 53 connected to a focuser 54. Collecting portion 55 may include a detector 56 connected to an analyzer 57, with the analyzer 57 connected to a lens collector 58. As will be appreciated and understood by one skilled in the art, a laser light may be polarized by a polarizer, such that the laser light is emitted in a specific and known polarized state when emitted onto a sample. In other words, the polarizer sets the polarization of the light such that the polarization of the light is known when the light hits the sample. The focuser may focus the light. A collector may be considered a counterpart to the focuser, where light reflected off of the sample is collected by the collector. In other words, the collector may be identical in form to the focuser, but instead of emitting light, the collector collects the reflected light. The collected light passes through another polarizer, which is referred to as an analyzer when collected light passes through it. The analyzer may be rotated to determine and map the polarization state of the reflected, i.e. collected, light. A detector may detect the intensity of the reflected light and the intensity may vary as a function of the angle of the analyzer. The above components of sensing unit 31 may be connected using, for example, optical fibers 70. Metrology system 30 may measure, for instance, one or more characteristics of wafer 80 at one or more point, region, or location on wafer 80. For instance, a single metrology system 30 may be included in wafer carrier system 10, for instance, secured to housing 20, and measure a point, a region, or a location on wafer 80. In other embodiments, for instance, multiple metrology system 30 may be included in wafer carrier system 10 and measure the corresponding number of point, region, or locations on wafer 80. The measurement may be taken at any point, region, or location on wafer 80 as needed or desired by, for instance, positioning focuser 54 and lens collector 58 over the portion of wafer 80, i.e. the point, region, or location on the wafer, where measurement will be taken. The portion of wafer 80 corresponding to the tips of focuser 54 and lens collector 58 may be referred to as measurement point 81.

Figure 4:
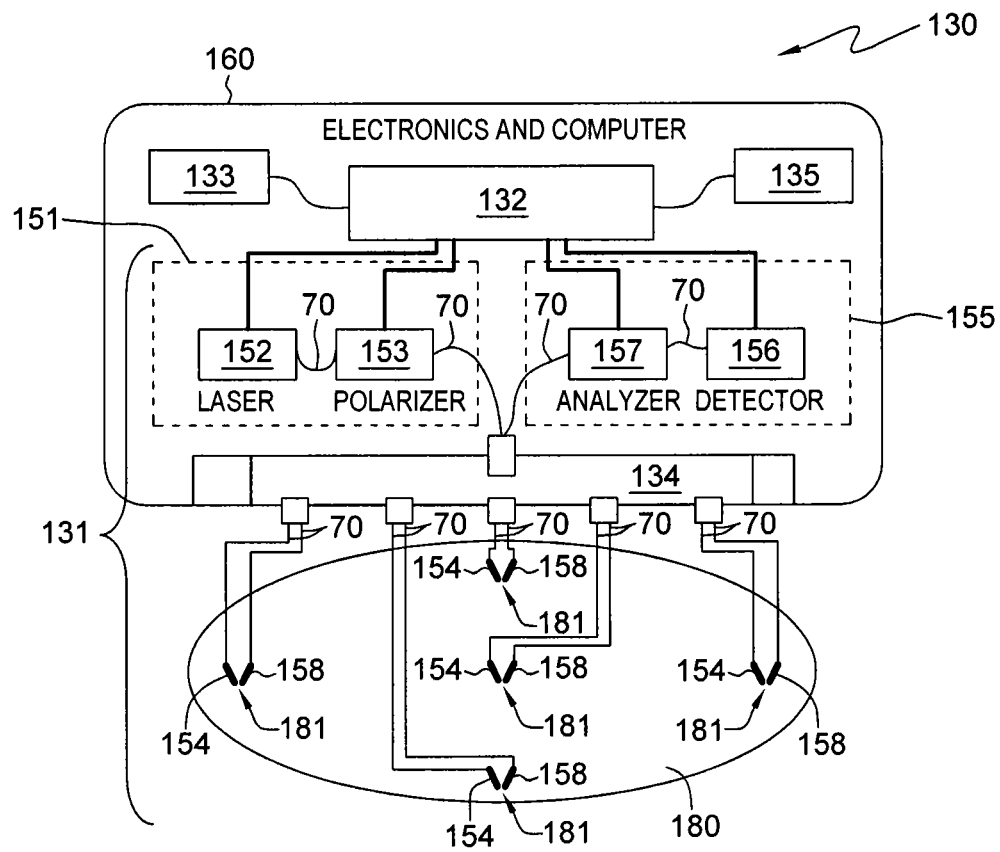
FIG. 4 is a schematic illustration of a metrology system for use in the wafer carrier system of FIG. 1, according to an embodiment of the present disclosure.

With reference to FIG. 4, in some embodiments, wafer carrier system 10 (FIG. 1) may include a metrology system 130 operable to measure multiple measurement points 181 on a wafer 180. Measurement point 181 may include the same or similar characteristics as measurement point 81 described above. For instance, measurement point 181 may refer to any point, region, or location on wafer 180, where measurement will be taken. Metrology system 130 may include an enclosure 160 disposed within housing 20 (FIG. 1). Enclosure 160 may be a wholly enclosed structure or may be a supporting frame, such as a chassis, and may include the same or similar features as enclosure 60 (FIG. 3) described above.

As depicted in FIG. 4, metrology system 130 includes a sensing unit 131 having, for example, an emitting portion 151, a collecting portion 155, and a multiplexer 134. Emitting portion 151 may include, for example, an emitter such as a laser 152 connected to a polarizer 153 that is connected to multiplexer 134. Collecting portion 155 may include, for example, a detector 156 connected to an analyzer 157 that is connected to multiplexer 134. The multiplexer may be a device, for instance, that selects one or more paths to forward an input signal from the emitting portion to the wafer. The multiplexer may also be a device, for instance, that selects one or more paths from the output signal from the wafer and forwards it to the collecting portion. Multiplexer 134 may allow, for example, multiple paths, e.g. the pairs of focusers and lens collectors, to share one set of the emitting portion 151 and one set of collecting portion 155. One or more pairs of a focuser 154 and a lens collector 158 may be operable for measuring one or more characteristics of wafer 180 at measuring points 181.

With reference still to FIG. 4, metrology system 130 may also include a computing unit 132 operably connected to sensing unit 131, and a power source 133 that powers computing unit 132 and sensing unit 131. Computing unit 132 may include the same or similar characteristics as computing unit 32 (FIG. 3). Metrology system 130 may also include a network adaptor 135 capable of sending and receiving data and control commands. For instance, after measuring one or more characteristics of wafer 180, the measurement data may be transmitted, for example, wirelessly to a remote computer 400 (FIG. 1). As described above, transmission of measurement data is not limited to wireless transmission and may be transmitted in any conventional manner. Network adaptor 135 may be a part of computing unit 132, for example, as an integrated component of computing unit 132, or may be operably connected to computing unit 132. Power source 133 may be, for example, a battery, which may be, for instance, rechargeable.

Figure 5:
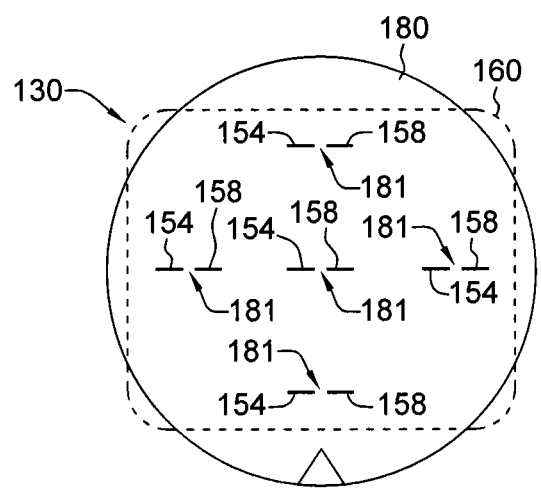
FIG. 5 is a schematic representation of a top view of the metrology system of FIG. 4 overlaying a wafer, illustrating various measurements points on the wafer.

FIG. 5 depicts a top-view of wafer 180 being measured and illustrates the position of metrology system 130 over wafer 180. The one or more characteristics of wafer 180 may be measured at one or more measurements points 181 on wafer 180. For instance, multiple measurements may be taken on various portions of wafer 180. Measurement points 181 may be on any portions of wafer 180, depending on the pattern or the number of measurements desired to be obtained, and is not limited to any particular pattern or number of measurements.

Figure 6:
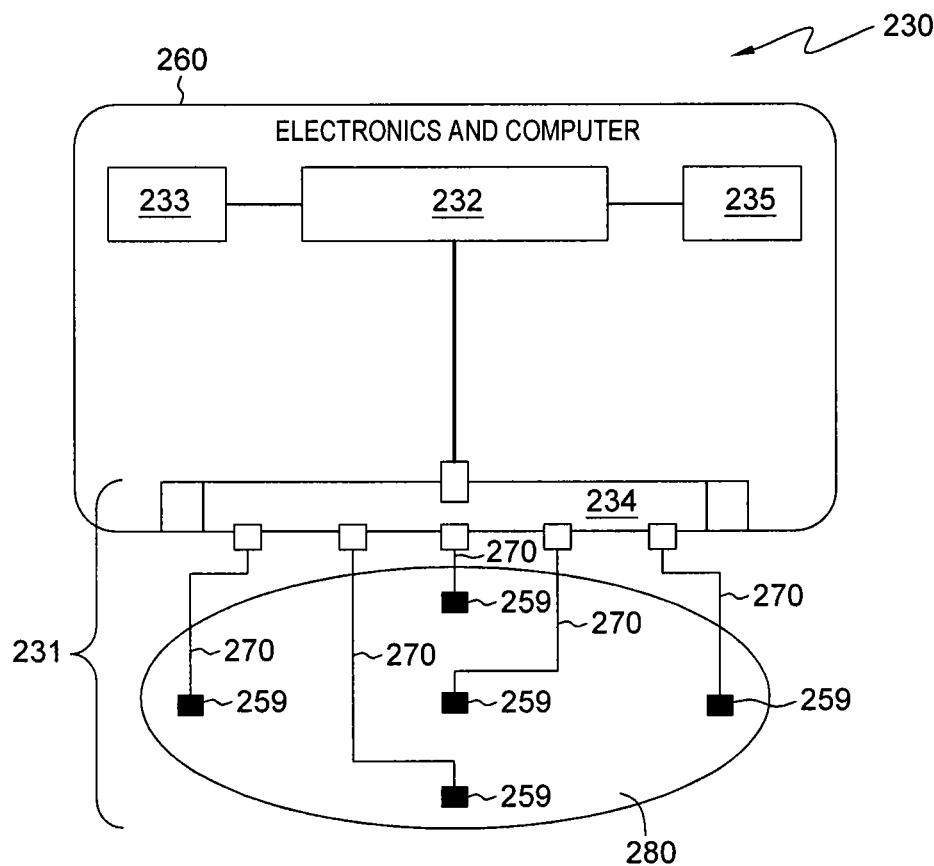
FIG. 6 is a schematic illustration a metrology system for use in the wafer carrier system of FIG. 1, according to an embodiment of the present disclosure.

With reference to FIG. 6, in some embodiments, wafer carrier system 10 (FIG. 1) may include a metrology system 230 that may include, for instance, a metrology instrument such as a pyrometer. Metrology system 230 may be disposed within an enclosure 260, which may be a wholly enclosed structure or may be a supporting frame, such as a chassis. Enclosure 260 may include the same or similar features as enclosure 60 (FIG. 4) described above. Metrology system 230 may include a sensing unit 231, a computing unit 232 connected to sensing unit 231, and a power source 233 that powers computing unit 232 and sensing unit 231. Computing unit 232 may include the same or similar characteristics as computing unit 32 (FIG. 3). Metrology system 230 may also include a network adaptor 235 capable of sending and receiving data and control commands. For instance, after measuring one or more characteristics of a wafer, the measurement data may be transmitted, for example, wirelessly to a remote computer 400 (FIG. 1). As described above, transmission of measurement data is not limited to wireless transmission and may be transmitted in any conventional manner. As also described above, network adaptor 235 may be a part of computing unit 232, for example, as an integrated component of computing unit 232, or may be operably connected to computing unit 232. Power source 233 may be, for example, a battery, which may be, for instance, rechargeable. Metrology system 230 may also include additional electronic components, which will be apparent to one skilled in the arts. Sensing unit 231 may include, for example, a multiplexer 234 and one or more probes 259 connected to multiplexer 234 by, for instance, electrical wires 270. In other embodiments, sensing unit 231 (not shown) may include a single probe, for example, an infrared camera with a wide angle lens to cover the entire wafer. In other embodiments, the metrology system may include an ellipsometer and/or reflectometer. With the use of a pyrometer, ellipsometer and/or reflectometer in a metrology system 230, film thickness, film temperature distribution of heat on the wafer, film composition, conductivity and reflectivity of the wafer surface, film optical constants, surface roughness, wafer topography, wafer bow, defects on the wafer surface, and the number of particles on the wafer surface, can be measured.

Figure 7:
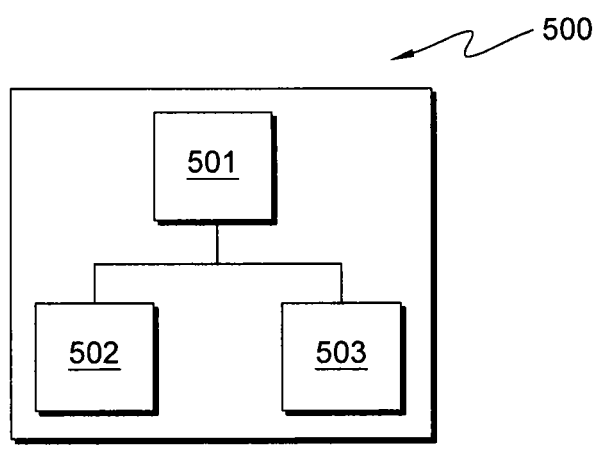
FIG. 7 is a schematic illustration of a computing unit according to an embodiment of the present disclosure.

FIG. 7 illustrates an example of a computing unit 500, for instance, computing unit 32 (FIG. 3), computing unit 132 (FIG. 4), or computing unit 232 (FIG. 6), that may be used in an embodiment of wafer carrier system 10 (FIG. 1). Computing unit 500 may include one or more processors 501, memory 502, and one or more input/output (I/O) devices 503, which may be coupled to each other by busses and other electrical hardware elements (not shown). Computing unit 500 may be, for example, a compact, fanless device. Processor(s) 501 may include any appropriate hardware component(s) capable of implementing functions, for instance executing instruction(s) (sometimes alternatively referred to as code, firmware and/or software) retrieved from memory 502. Memory 502 may include hardware components or other storage devices to store data, such as programs of instructions for execution, and other data. I/O devices 503 may include hardware and/or software components that support input and output of data to/from computing unit 500. I/O devices 503 may include physical components that attach physically or wireless to the computing unit and/or integrate into computing unit 500, for example, display devices, gyroscopes, light sensors, proximity sensors, and accelerometers. I/O devices 503 may also include, for example, communications links for passing data packets between the computing unit and other systems (e.g. remote computer 400 (FIG. 1)) across one or more networks, such as the Internet or intranet. Other example I/O devices 503 may include universal serial bus (USB), peripheral component interconnect (PCI), and serial adapters/interfaces configured to couple to devices of their respective kind.

Figure 8:
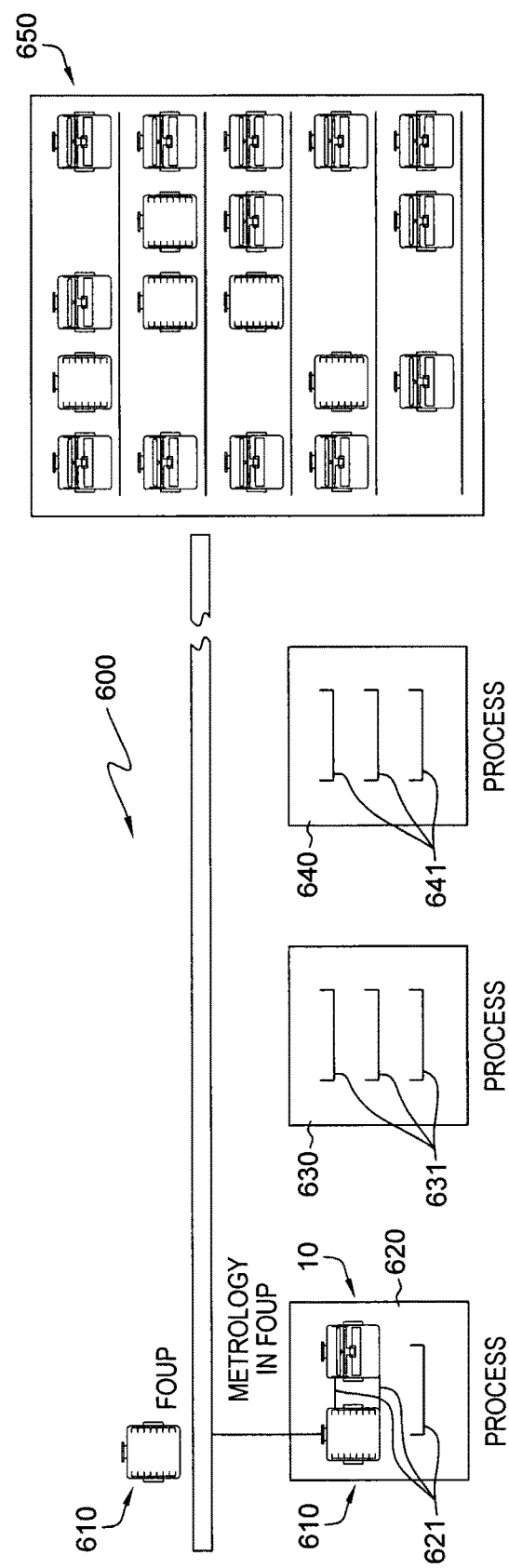
FIG. 8 is a schematic illustration of the wafer carrier system in use in an automated fab according to an embodiment of the present disclosure.

FIG. 8 depicts a schematic illustration of wafer carrier system 10 in use in an automated fab with an AMHS 600, according to one embodiment of the present disclosure. Wafer carrier system 10 may be mounted on a load port 621 of a first process station 620. A standard FOUP 610, i.e. a wafer carrier that does not include a metrology system, may be mounted on load port 621 next to wafer carrier system 10. After processing at a first processing station 620, wafer(s) may be moved, for example, by an automated tool or robot into wafer carrier system 10 to measure one or more characteristics of wafer(s) 80, for example, while wafer carrier system 10 remains mounted on load port 621. After being measured, wafer(s) may be moved by, for example, an automated tool or robot back into standard FOUP 610, for example, for transporting to another processing station, such as a second processing station 630, or a storage unit 650, also referred to as stocker.

In some embodiments, wafer(s) may remain in wafer carrier system 10 and be measured while being transported to another location, such as a second process station 630, a third processing station 640, or storage unit 650, or while awaiting an action, for instance, while on a load port 631 of second process station 630 prior to processing at second process station 630, or while in storage unit 650.

Thus, in accordance with the present disclosure, wafer carrier system 10, which measures one or more characteristics of the wafers, may be located at various different locations within an automated material handling system 600 and/or a fab. For example, wafer carrier system 10 may be located adjacent a first processing station 620, which performs a first process on a semiconductor wafer. Wafer carrier system 10 may also be disposed on a load port 621 of the first processing station 620, or otherwise located proximate to first processing station 620. After such process, the wafer may be moved into wafer carrier system 10 wherein one or more characteristics of the wafer are measured. The measured characteristic may be film thickness, film temperature, heat distribution on the wafer, film composition, electrical conductivity, film optical constants, surface roughness, wafer topography, wafer bow, defects on the wafer surface, number of particles on the wafer surface, and/or reflectivity on the surface of the wafer. Each of these measurements may be conducted by a separate wafer carrier system 10 with a metrology system 30 therein. Accordingly, depending upon the characteristics measured, either one or multiple wafer carrier systems may be located adjacent first processing station 620. Similarly, adjacent a second process station 630, another wafer carrier system 10 may be used. The wafer carrier systems near second process station 630 may be also capable of measuring one or more of the aforementioned characteristics. Each wafer carrier system may be capable of measuring one or multiple of the aforementioned characteristics. Similarly, the wafer carrier system 10 may be located at other processing stations within a semiconductor wafer automated material handling system.

Accordingly, in aspects of the disclosure, an AMHS for an automated semiconductor fabrication facility may include wafer carrier systems 10 as described previously herein. Such wafer carrier systems may be located at various locations along the semiconductor wafer AMHS either adjacent individual process stations, namely, in processing stations, before processing stations or after processing stations, as well as along transport lines between processing stations, and at storage locations for semiconductor wafers.

Figure 9:
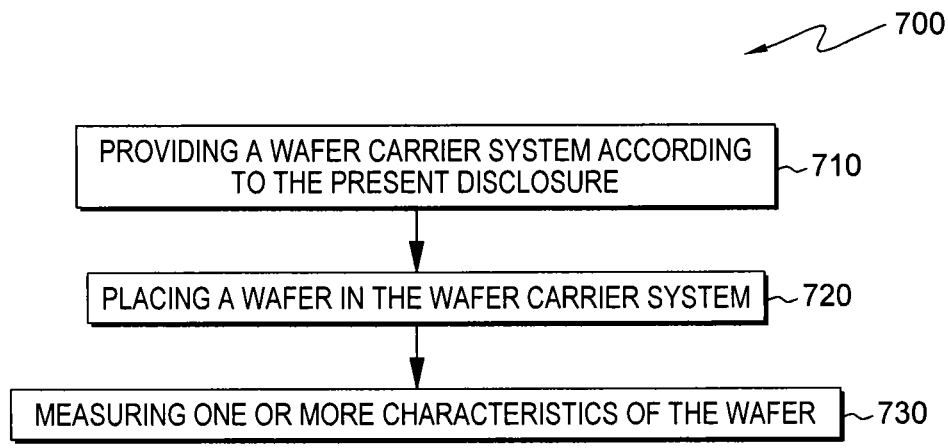
FIG. 9 is a flowchart of a method of measuring one or more characteristics of a semiconductor wafer according to an embodiment of the present disclosure.

With reference to FIG. 9, in one embodiment, a method 700 for measuring one or more characteristics of a semiconductor wafer is disclosed. The method 700 includes at 710 providing a wafer carrier system according to the present disclosure, at 720 placing a wafer in the wafer carrier system, and at 730 measuring one or more characteristics of the wafer.

Figure 10:
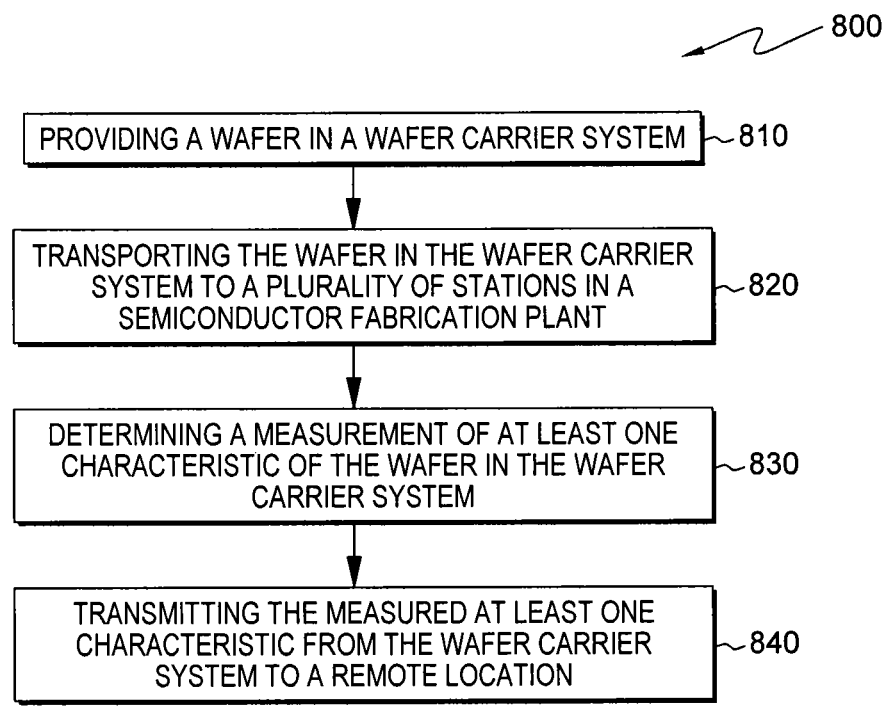
FIG. 10 is a flowchart of a method of measuring one or more characteristics of a semiconductor wafer according to an embodiment of the present disclosure.

With reference to FIG. 10, in one embodiment, a method 800 for measuring one or more characteristics of a semiconductor wafer is disclosed, method 800 includes at 810 providing a wafer in a wafer carrier system, at 820 transporting the wafer in the wafer carrier system to a plurality of stations in a semiconductor fabrication plant, at 830 determining a measurement of at least one characteristic of the wafer in the wafer carrier system, and at 840 transmitting the measured at least one characteristic from the wafer carrier system to a remote location.

As will be appreciated, the wafer carrier systems of the present disclosure will not be disruptive to the AMHS implemented in any existing fab environment and may improve overall efficiency of manufacturing semiconductor devices. Cycle time may be beneficially reduced by, for instance, eliminating the transport time of moving wafers directly from one processing station to the next processing station, rather than transporting wafers to metrology stations after a processing step. Another benefit may be realized by performing metrology on wafers shortly after processing and matching the maturity of process. Costs may also be reduced, for instance, as multiple, expensive metrology tools may not be necessary and as a result, such tools need not be occupying any cleanroom space. Additionally, the components of the wafer carrier systems are relatively inexpensive and maximize the use of automated systems to reduce labor costs. Wafer carrier systems of the present disclosure may also be shared across numerous tools, further promoting efficiency in costs and processing.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of one or more aspects of the disclosure and the practical application, and to enable others of ordinary skill in the art to understand one or more aspects of the disclosure for various embodiments with various modifications as are suited to the particular use contemplated.

The invention claimed is:

1. A semiconductor wafer carrier system transportable by an automated material handling system to a plurality of stations, the semiconductor wafer carrier system comprising:

a housing configured and engageable with the automated material handling system for transport by the automated material handling system to the plurality of stations, the housing comprising a wholly enclosed enclosure, a support positioned within the enclosure configured to support a semiconductor wafer within the enclosure, and a base, operably attached to the housing and a platform, including at least one micro motion motor configured to move the platform and the semiconductor wafer positioned thereon with respect to the sensor; and a sensor, operably attached to the housing and positioned at least partially within the enclosure, for obtaining data regarding the semiconductor wafer in the enclosure; and a device, operably attached to the housing, for use in forwarding the data regarding the semiconductor wafer in the enclosure to a remote location, wherein the housing comprises at least one of a handle and an adapter configured to engage with the automated material handling system to transport the semiconductor wafer carrier system by the automated material handling system to the plurality of stations.

2. The system of claim 1, wherein the device comprises a wireless transmitter.

3. The system of claim 2 further comprising a power source, operably attached to the housing, for powering the wireless transmitter.

4. The system of claim 1 further comprising a computing unit operably attached to the housing and to the sensor.

5. The system of claim 4 further comprising a power source, operably attached to the housing, for powering the computing unit.

6. The system of claim 4, wherein the device comprises a network adaptor operably connected to the computing unit.

7. The system of claim 1 further comprising a power source, operably attached to the housing, for powering at least one of the sensor and the device.

8. The system of claim 7, wherein the power source comprises a battery.

9. The system of claim 1 further comprising a metrology system operably attached to the housing comprising the sensor, and wherein the data forwarded comprises a measurement of at least one characteristic of the semiconductor wafer.

10. The system of claim 1, wherein the sensed data is relatable to film thickness, film temperature, distribution of heat on the wafer, film composition, electrical conductivity, film optical constants, surface roughness, wafer topography, wafer bow, defects on the wafer surface, number of particles on the wafer surface, and reflectivity of the surface of the wafer.

11. The system of claim 1, wherein the sensor comprises one or more of an ellipsometer, a reflectomer, and a pyrometer.

12. The system of claim 1, wherein the sensor comprises a plurality of probes, and further comprising:
   a multiplexer operably connected to the plurality of probes; and
   wherein each of the plurality of probes are operable for use in obtaining data regarding the semiconductor wafer.

13. The system of claim 1, wherein the sensor comprises:
   an emitting portion; and
   a collecting portion.

14. The system of claim 13, wherein:
   the emitting portion comprising:
      a laser;
      a polarizer operably connected to the laser; and
      a focuser operably connected to the polarizer; and
   the collecting portion comprising:
      a detector;
      an analyzer operably connected to the detector; and
      a lens collector operably connected to the analyzer; and wherein the focuser and the lens collector are operable for use in measuring a portion of the semiconductor wafer.

15. The system of claim 13, further comprising a multiplexer operably connected to the emitting portion and the collecting portion, and wherein:
   the emitting portion comprises:
      a laser; and
      a polarizer operably connected to the laser; and
   the collecting portion comprises:
      a detector; and
      an analyzer operably connected to the detector; and
   wherein the multiplexer is operably connected to the polarizer and the analyzer, the multiplexer having a plurality of focusers and lens collectors.

16. The system of claim 1, wherein the housing comprises a front door.

17. A method comprising:
   providing the semiconductor wafer carrier system of claim 1;
   placing a semiconductor wafer in the semiconductor wafer carrier system;
   sensing data regarding the semiconductor wafer; and
   forwarding data regarding the sensed semiconductor wafer in the enclosure to the remote computer.

18. A semiconductor wafer carrier system transportable by an automated material handling system to a plurality of stations, the semiconductor wafer carrier system comprising:
   a housing configured and engageable with the automated material handling system for transport by the automated material handling system to the plurality of stations, the housing comprising a wholly enclosed enclosure and a support positioned within the enclosure configured to support a semiconductor wafer within the enclosure; and
   a sensing unit, operably attached to the housing and positioned at least partially within the enclosure, for obtaining data regarding the semiconductor wafer in the enclosure; and
   a power source, operably attached to the housing, for powering the sensor,
   wherein the housing comprises at least one of a handle and an adapter configured to engage with the automated material handling system to transport the semiconductor wafer carrier system by the automated material handling system to the plurality of stations, and
   wherein the housing further comprises a base, operably attached to the housing and a platform, including at least one micro motion motor configured to move the platform and the semiconductor wafer positioned thereon with respect to the sensing unit.

19. The system of claim 18, further comprising a device, operably attached to the housing, for use in forwarding the data regarding the semiconductor wafer in the enclosure to a remote location, and a computing unit operably attached to the housing, and wherein the power source is operable to power the device and computing unit.

* * * * *